United States Patent
Aberg et al.

(10) Patent No.: US 9,345,697 B2
(45) Date of Patent: *May 24, 2016

(54) METHODS OF TREATMENT OF NON-HISTAMINIC PRURITUS

(71) Applicant: BRIDGE PHARMA, INC., Sarasota, FL (US)

(72) Inventors: A. K. Gunnar Aberg, Sarasota, FL (US); Vincent B. Ciofalo, Branford, CT (US)

(73) Assignee: BRIDGE PHARMA, INC., Sarasota, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/736,626

(22) Filed: Jun. 11, 2015

(65) Prior Publication Data

US 2015/0272942 A1    Oct. 1, 2015

Related U.S. Application Data

(63) Continuation-in-part of application No. 13/960,114, filed on Aug. 6, 2013, now Pat. No. 9,138,431.

(51) Int. Cl.
*A01N 43/40* (2006.01)
*A61K 31/445* (2006.01)
*A61K 31/4535* (2006.01)
*A61K 9/00* (2006.01)

(52) U.S. Cl.
CPC ........... *A61K 31/4535* (2013.01); *A61K 9/0053* (2013.01)

(58) Field of Classification Search
None
See application file for complete search history.

(56) References Cited

U.S. PATENT DOCUMENTS

| | | | |
|---|---|---|---|
| 3,682,930 | A | 8/1972 | Bourquin et al. |
| 5,595,997 | A | 1/1997 | Aberg et al. |
| 6,207,683 | B1 | 3/2001 | Aberg et al. |
| 6,207,684 | B1 | 3/2001 | Aberg |
| 7,226,934 | B1 * | 6/2007 | Aberg ............... C07D 409/04 514/324 |
| 7,557,128 | B2 | 7/2009 | Aberg et al. |
| 8,557,846 | B1 | 10/2013 | Aberg et al. |
| 9,138,431 | B2 | 9/2015 | Aberg et al. |
| 2010/0105734 | A1 | 4/2010 | Aberg et al. |
| 2010/0130550 | A1 | 5/2010 | Aberg et al. |
| 2015/0045392 | A1 | 2/2015 | Aberg et al. |
| 2015/0342944 | A1 | 12/2015 | Aberg et al. |

FOREIGN PATENT DOCUMENTS

| | | |
|---|---|---|
| WO | 0119367 A1 | 3/2001 |
| WO | 03057919 A2 | 7/2003 |
| WO | 2014066212 A1 | 5/2014 |

OTHER PUBLICATIONS

Abila et al.; "Effects of Clemastine, Ketotifen and Prednisolone on Chloroquine-induced Pruritus"; J Trop Med Hyg.; 92(5); pp. 355-359; (1989) Abstract only.
Adebayo et al.; "Chloroquine-induced Pruritus in Malaria Fever: Contribution of Malaria Parasitaemia and the Effects of Prednisolone, Niacin, and their Combination, Compared with Antihistamine"; Br J Clin Pharmacol; 44; pp. 157-161; (1997).
Autoimmunity from IDF Patient & Family Handbook for Primary Immunodeficiency Diseases Fifth Edition by Immune Deficiency Foundation; http://primaryimmune.org/about-primary-immunodeficiencies/relevant-info/autoimmunity/; 9 pages; printed May 2015.
Brown et al.; "Atopic and Non-atopic Eczema Clinical Review"; BMJ; 332; pp. 584-588; (2006).
Cevikbas et al.; "A Sensory Neuron-expressed Interleukin-31 Receptor Mediates T Helper Cell-dependent Itch: Involvement of TRPV1 and TRPA1"; J Allergy Clin Immunol; 133(2); pp. 448-460; (2014).
Ellis, Carolyn; "Notalgia Paresthetica: The Unreachable Itch"; Dermatol Pract Concept; 3(1): pp. 3-6; (2012).
Fleck, et al.; "Comparison of the Janus Kinase (JAK) Inhibitor, Oclacitinib, and Prednisolone in Canine Models of Pruritus"; Veterinary Dermatology; 23 (Suppl. 1); 38; (2012); abstract only.
Kasutani et al.; "Anti-IL-31 Receptor Antibody Is Shown to be a Potential Therapeutic Option for Treating Itch and Dermatitis in Mice"; British Journal of Pharmacology; 171; pp. 5049-5058; (2014).
Leung et al.; "Atopic Dermatitis"; Lancet; 361; pp. 151-160; (2003).
Liu et al.; "Cloning and Pharmacological Characterization of a Fourth Histamine Receptor (H4) Expressed in Bone Marrow"; Molecular Pharmacology; 59; pp. 420-426; (2001).
Liu et al.; "Sensory Neuron-Specific GPCR Mrgprs Are Itch Receptors Mediating Chloroquine-Induced Pruritus"; Cell; 139; pp. 1353-1365; (2009).
Nobbe et al.; "IL-31 Expression by Inflammatory Cells is Preferentially Elevated in Atopic Dermatitis"; Acta Derm Venereol; 92; pp. 24-28; (2012).
Oaklander, Anne Louise; "Neuropathic Itch"; Semin Cutan Med Surg; 30(2); pp. 87-92 (2011).
Osifo, Nosakhare Guy; "Structure Activity Relationships in the Pruritogenicity of Chloroquine and Amodiaquine Metabolites in a Dog Model"; Jounral of Dermatological Science; 2; pp. 92-96; (1991).

(Continued)

*Primary Examiner* — Dennis Heyer
*Assistant Examiner* — Daniel M Podgorski
(74) *Attorney, Agent, or Firm* — Cantor Colburn LLP

(57) ABSTRACT

Described herein are methods of treating a mammal in need of treatment for non-histaminic pruritus by administering to the mammal in need thereof a therapeutically effective amount of RS-norketotifen or a pharmaceutically acceptable salt thereof, thereby reducing the desire to scratch in the mammal. Non-histaminergic types of pruritus are resistant to treatment with selective histamine H-1-, H-2- and H-4-receptor inhibitors. In certain aspects, the non-histaminergic pruritus is associated with a dermal disorder, a psychological disorder, a mental disorder, a nerve disorder, or a systemic disorder.

10 Claims, No Drawings

(56) References Cited

OTHER PUBLICATIONS

Papoiu et al.; "Cowhage-Induced Itch as an Experimental Model for Pruritus. A Comparative Study with Histamine-Induced Itch"; PLoS One; 6(3); e17786; (2011) retrieved on-line www.ncbi.nlm.nih.gov/pmc/articles/PMC3056722/pdf/pone.0017786.pdf.
Patel et al.; "Therapy of Pruritus"; Expert Opinion Pharmacother; 11; pp. 1673-1682; (2010).
Sampogna et al.; "Prevalence of Symptoms Experienced by Patients with Different Clinical Types of Psoriasis"; Br J Dermatol; 151(3); pp. 594-599; (2004); abstract only.
Schulz et al.;"A Common Haplotype of the IL-31 Gene Influencing Gene Expression is Assocaited with Nonatopic Eczema"; J Allergy Clin Immunol; 120(5); pp. 1097-1102; (2007).
Stander et al.; "Prevalence of Chronic Pruritus in Germany: Results of a Cross-sectional Study in a Sample Working Population of 11,730"; Dermatology; 221; pp. 229-235; (2010); abstract only.
Steinhoff et al.; "Proteinase-Activated Receptor-2 Mediates Itch: A Novel Pathway for Pruritus in Human Skin"; The Journal of Neuroscience; 23(15); pp. 6176-6180; (2003).
Storan et al.; "Role of Cytokines and Chemokines in Itch"; pp. 163, 166-170, 173-176; in Pharmacology of Itch. Handbook of Experimental Pharmacology; 226; Eds. Cowan A and Yosipovitch G, Springer-Verlag, (2015).
Taylor et al.; "Pruritus"; Cleveland Clinic_Center for Continuing Education; http://www.clevelandclinicmeded.com/medicalpubs/diseasemanagement/dermatology/pruritus-itch/Default.htm; printed Aug. 2010.
Venereau et al.; "Definition and Characterization of an Inhibitor for Interleukin-31"; J Biol Chem.; 285; pp. 14955-14963; (2010).
Wilson et al.; "TRA1 is Required for Histamine-independent, Mas-related G Protein-coupled Receptor-mediated Itch"; Nat Neurosci; 14(5); pp. 595-602; (2011).
Cheng et al.; "Relationship Between the Inhibition Constant (K1) and the Concentration of Inhibitor Which Causes 50 Per Cent Inhibition (I50) of an Enzymatic Reaction"; Biochemical Pharmacology; 22; pp. 3099-3108; (1973).
Deml et al.; "Interactions of Histamine H1-Receptor Agonists and Antagonists with the Human Histamine H4-Receptor"; Molecular Pharmacology; 76; pp. 1019-1030; (2009).
Waldvogel et al.; Untersuchungen uber synthetische Arzneimittel 9- und 10-Oxo-Derivate von 9,10-Dihydro-4H-benzo[4,5]cyclohepta-[1,2-b]thiophenen, Helvetica Chimica Acta, 59; pp. 866-877; (1976) with English abstract.

* cited by examiner

METHODS OF TREATMENT OF NON-HISTAMINIC PRURITUS

CROSS-REFERENCE TO RELATED APPLICATIONS

This application is a continuation in part of U.S. application Ser. No. 13/960,114 filed on Aug. 6, 2013, which is incorporated herein by reference in its entirety.

TECHNICAL FIELD

The embodiments disclosed herein relate to methods of norketotifen-treatment of pruritus that is mediated through non-histaminergic pruritic mechanisms in mammals.

BACKGROUND

Pruritus is also called itch. Pruritus (like pain) is not a disease, but a symptom of a disease (condition, disorder) that causes the expression of pruritus. Thus, pruritus (like pain) is a warning signal, telling the patient that some underlying disorder is present. The terms "condition", "disease", and "disorder" are synonyms and are often called "underlying condition", "underlying disease" or "underlying disorder" in connection with pain or pruritus.

Pruritus is an unpleasant sensation that elicits the desire to scratch. Acute pruritus is a frequent experience in most mammalian species and can usually be abolished by scratching at the area of the itching. Chronic pruritus can be debilitating and scratching provides no or very little relief; actually, scratching most often exacerbates the problem. As used herein, the terms "pruritus", "pruritic", "itch", "itching" etc. refer to chronic pruritus.

Pruritus is experienced by many mammals, including humans. Pruritus in humans can be caused by various underlying diseases, such as for example dermatological disorders, neurological disorders, systemic disorders and by drugs with pruritic side effects. Pruritus in dogs is also common and usually caused by parasites, various allergens or underlying diseases. Canine pruritus is rarely successfully treated with antihistamines. Thus pruritic dogs almost exclusively suffer from non-histaminergic itch. Pruritus in cats is usually caused by parasites or allergens or other conditions. Cats react to itchiness in similar ways as dogs. Thus, both cats and dogs are scratching, licking and biting. However, contrary to dogs, up to 50 percent of cats with pruritus seem to have histamine-sensitive types of pruritus, while the remaining pruritic cats suffer from non-histaminergic forms of pruritus. Pruritus in horses is very common and is one of the most common reasons for horse owners to seek help from veterinarians. A horse with itchy skin will rub up against fences, stalls, trees, or other objects while attempting to scratch the itch. The horse may excessively bite or lick its skin to the point of causing bleeding or damage to the skin. The most common causes of allergic itching in horses are insect bites, food allergies including allergens in horse feed, and itching due to seasonal allergens. Pruritus in horses is seldom treated successfully with antihistamines, indicating that pruritus in horses usually is non-histaminergic pruritus.

The lack of success of antihistamines in treating pruritus suggests that treatments for non-histaminergic pruritus are needed across species.

Patients suffering from histamine-induced pruritus can be treated with inhibitors (inverse agonists) of histamine H-1 receptors, such as for example desloratadine or diphenhydramine, or by histamine H-2 receptor inhibitors, such as for example cimetidine and ranitidine, or—when they become commercially available—by histamine H-4 receptor inhibitors, such as for example JNJ 7777120. Such treatments, however, are ineffective in the treatment of non-histaminergic pruritus.

Human patients suffering from non-histaminergic pruritus usually try medications, such as corticosteroids, antiepileptic drugs, opioid receptor antagonists, antidepressants or local anesthetics to relive itch, however, such medications are relatively unsuccessful. In addition, the anti-epileptic drug gabapentin, which impedes signals transmitting pain and pruritus to the brain, may offer some relief for human patients who can withstand the severe adverse events caused by this drug.

What is needed are treatments for non-histaminergic pruritus that are both effective and free from debilitating side effects.

SUMMARY

In one aspect, disclosed herein is a method of treating a mammal in need of treatment for non-histaminergic pruritus, comprising orally or topically administering to the mammal in need thereof a therapeutically effective amount of RS-norketotifen or a pharmaceutically acceptable salt thereof. In specific embodiments, administration of the therapeutically effective amount of norketotifen or a pharmaceutically acceptable salt thereof is expected to avoid systemic adverse drug effects, because the orally administered amount of RS-norketotifen accumulates in the skin where pruritus is expressed as a symptom for numerous underlying diseases. In certain aspects, the non-histaminergic pruritus is associated with a dermal disorder, a psychological disorder, a mental disorder, a nerve disorder, or a systemic disorder.

In another aspect, a method of treating a mammal in need of treatment for non-histaminergic pruritus is described and comprises orally administering to the mammal in need thereof a therapeutically effective amount of a biophase-selective inhibitor of non-histaminergic pruritus, wherein the biophase-selective non-histaminergic antipruritic drug is norketotifen, or an isomer of norketotifen, or a pharmaceutically acceptable salt of racemic or isomeric norketotifen.

DETAILED DESCRIPTION

Pruritus (itch) is a sensation that causes the desire or reflex to scratch. Pain and pruritus have anatomical and physiological similarities, but while pain evokes a withdrawal reflex, pruritus creates a scratching reflex. Therefore scratching is a symptom caused by an underlying disease (condition, disorder). Often multiple scratches are evoked, usually called "bouts of scratches".

Table 1 lists diseases causing pruritus, of which diseases marked with (*) are always or most often caused by non-histaminic mechanisms. Information that concerns clinical use of histamine H-4 inhibitors in Table 1 refers to anticipated use since no orally active histamine H-4 receptor inhibitors have yet obtained regulatory approved for clinical use.

TABLE 1

Examples of underlying conditions that cause pruritus in human patients and effects of antihistaminic drugs on the various forms of pruritus A. Examples of Dermatological Disorders Causing Chronic Pruritus

| | |
|---|---|
| Autoimmune disorders | Atopic dermatitis - histaminergic (H-4) or non-histaminergic (*)<br>Dermatitis herpetiformis - antihistamine-resistant (*)<br>Dermatomyositis - most often antihistamine-resistant (*)<br>Pemphigoid - antihistamine are ineffective (*)<br>Psoriasis - histaminergic (H-4) or non-histaminergic (*)<br>Sjögren's syndrome - antihistamines contraindicated |
| Genetic disorders | Darier's disease - antihistamines are being used<br>Hailey-Hailey disease - minimal effect of antihistamines (*)<br>Ichthyosis - minimal or no effect of antihistamines (*) |
| Infections and Infestations | Arthropod reactions - antihistamines or combinations of H-1 and H-2 inhibitors are used for bee-sting; steroids if patient is allergic<br>Dermatophytosis - mostly antihistamine-resistant (*)<br>Bacterial infections - histamine H-4 inhibitors to be used<br>Folliculitis - histamine H-4 inhibitors to be used<br>Fungal infections - histamine H-4 inhibitors to be used<br>Impetigo and other bacterial infections - H-4 antihistamines to be used<br>Pediculosis - histamine H-4 inhibitors to be used<br>Scabies - histamine H-4 inhibitors to be used<br>Viral infections - histamine H-4 inhibitors to be used |
| Inflammatory disorders | Asteatosis - no or minimal effect of antihistamines (*)<br>Atopic and non-atopic dermatitis - histaminergic (H-4) or non-histaminergic (*)<br>Contact dermatitis - histamine H-4 inhibitors to be used<br>Lichen planus - antihistamines are used<br>Lichen simplex chronicus - Gen-1 antihistamines are used<br>Mastocytosis - H-1 and H-2 antihistamines are used<br>Miliaria - antihistamines are used for pruritus caused by heat rash<br>Psoriasis - Histaminergic (H-4) or non-histaminergic (*)<br>Scars - non-sedating antihistamines have no or minimal effect (*)<br>Urticaria - Gen-1 antihistamine + H-2 antihistamines are used |
| Neoplastic disorders | Cutaneous B-cell lymphoma - no/minimal effect of antihistamines (*)<br>Cutaneous T-cell lymphoma - no/minimal effect of antihistamines (*)<br>Leukemia cutis - not antihistamines but gabapentin (*) |

B. Examples of Systemic Disorders causing Chronic Pruritus

Anemia - antihistamines have no or minimal effect (*)
Cholestatic diseases - may respond to antihistamines
Chronic renal failure - no or minimal effect of antihistamines (*)
Diabetes mellitus - often resistant to antihistamines (*)
Hyperthyroidism - often resistant to antihistamines (*)
Hypothyroidism - often resistant to antihistamines (*)
Renal failure - resistant to antihistamines (*)
Uremia - resistant to antihistamines (*)

C. Examples of Psychological or Mental Disorders causing Chronic Pruritus

Anxiety - no or minimal effects of non-sedating antihistamines (*)
Depression - antihistamines have no or minimal effect (*)
Stress - non-sedating antihistamines have no or minimal effect (*)
Neuropathic itch - antihistamine are ineffective (*)
Neuroses - Gen-1 antihistamines have no or minimal effect (*)
Psychoses - Gen-1 antihistamines have no or minimal effect (*)

D. Examples of Nerve Disorders causing Chronic Pruritus

Multiple sclerosis - antihistamines have no or minimal effect (*)
Diabetes mellitus - antihistamines have no effect (*)
Neuropathic itch - antihistamines have no effect (*)
Postherpetic neuralgia no or minimal effect of antihistamines (*)

E. Examples of Drugs causing Chronic Pruritus

ACE-inhibitors - resistant to antihistamines (*)
Allopurinol - resistant to antihistamines (*)
Amiodarone - resistant to antihistamines (*)
Chloroquine - resistant to antihistamines (*)
Estrogen - resistant to antihistamines (*)
Hydrochlorothiazide - resistant to antihistamines (*)
Hydroxyethyl cellulose - resistant to antihistamines (*)
Opioids - resistant to antihistamines (*)
Simvastatin - resistant to antihistamines (*)

Pruritus that does not respond to treatment with antihistaminic drugs (histamine H-1, H-2 or H-4 receptor inhibitors), is called non-histaminergic pruritus and the treatment of non-histaminergic pruritus with RS-, R- and S-norketotifen is the subject of this application. An underlying disease, such as for example atopic dermatitis or psoriasis, may express histaminergic pruritus in some patients and non-histaminergic pruritus in other patients.

Non-histaminergic pruritus can be caused by various diseases such as for example, renal failure, cholestasis, dermal and/or systemic infections, endocrine disorders, neurological disorders, malignancies, psychological disorders, various medications and various dermal disorders. The diagnosis by the doctor or veterinarian may be "idiopathic pruritus" which term is misleading, since it is the underlying disease—not the symptom that is idiopathic, which means that said underlying disease has not been diagnosed. Pruritus associated with idiopathic disorders, such as for example "idiopathic dermatitis" may in some patients be non-histaminergic pruritus which means that the itching is resistant to treatment with histamine inhibitory drugs. Idiopathic Dermatitis may in other patients express pruritus that is responsive to treatment with histamine H-1-, histamine H-2 and histamine H-4 receptor inhibitors. Regardless if the underlying disease has been diagnosed or not, non-histaminergic itching is often very severe, has a strong negative impact on the patient's quality of life and need immediate and chronic treatment.

In one aspect, to determine if the mammalian patient is suffering from non-histaminergic pruritus, the medical doctor or the veterinarian will test if said patient reacts positively to treatment with a selective histamine H-1 receptor inhibitor, such as for example diphenhydramine or desloratadine, and a selective histamine H-2 receptor inhibitors, such as for example cimetidine or ranitidine, and a selective histamine H-4 receptor inhibitor, such as for example JNJ7777120 or JNJ 10191584. If the patients is not relieved from pruritus with these treatment, the caregiving doctor or veterinarian can conclude that the patient suffers from non-histaminic pruritus and may obtain antipruritic benefit from treatment with the therapeutic dose of the non-histaminergic antipruritic drug RS-norketotifen.

Pruritus associated with psychological or mental disorders may in some human patients be associated with histaminergic pruritus, but other human patients suffer from non-histaminergic pruritus that is associated with psychological or mental disorders. The non-histaminergic pruritus in these patients can be associated with conditions such as for example anxiety, depression, emotional stress, neuroses, psychological trauma and psychoses. Pruritus associated with nerve disorders may in some human patients be associated with histaminergic pruritus, but other human patients may suffer from non-histaminergic pruritus that is associated with underlying conditions that have been determined to be nerve disorders, such as for example diabetes mellitus, multiple sclerosis, neuropathic diseases, scars, and post-herpetic neuralgias.

Pruritus associated with systemic disorders may in some patients be associated with histaminergic pruritus, but other patients suffer from non-histaminergic pruritus that is associated with various systemic disorders, such as for example anemia, diabetes, Hodgkin lymphoma, iron deficiency, chronic renal failure, systemic scleroderma, multiple sclerosis, uremia, and conditions such as pregnancy.

Pruritus associated with a dermal disorders, are in many cases non-histaminic pruritus and associated with diseases such as for example alopecia areata, asteatotic dermatitis, atopic dermatitis, cutaneous B-cell lymphoma, cutaneous T-cell lymphoma, dermatitis herpetiformis, discoid eczema, hand eczema, ichthyosis, mycosis fungoides, neurodermatitis, non-atopic dermatitis, notalgia paresthetica, psoriasis, prurigo nodularis, seborrheic dermatitis, Sézary syndrome and varicose eczema.

"Atopic dermatitis" and "non-atopic dermatitis" are different diseases, albeit classified as two types of dermatitis. There is no pathognomonic sign that differentiates between the diseases. Patients with atopic dermatitis most often have IgE-mediated sensitivity to allergens and are mostly children, while patients with non-atopic dermatitis do not have IgE-mediated dermatitis and are mostly adults. Importantly, both pruritus associated with atopic dermatitis and pruritus associated with non-atopic dermatitis are practically exclusively non-histaminic forms of pruritus.

Pruritus has been found to be the most frequent complaint (64%) among patients suffering from psoriasis. Psoriatic pruritus does not respond to antihistaminic drugs and is a non-histaminic symptom of psoriasis.

Antihistamines are used to treat a variety of conditions, in general those that involve histamine receptors. It is well known to those skilled in the art of pharmacology that antihistamines are inverse agonists that reverse the constitutive activity of histamine receptors. For the sake of simplicity, said inverse agonists are herein referred to as receptor inhibitors or as antihistamines.

In order to diminish the pruritus, the physician or veterinarian will attempt to determine the underlying condition that is causing the itching and treat the underlying condition. However, in many cases, identification of the underlying condition is not possible and the underlying disease is therefore referred to as being idiopathic. In such cases, or when treatment of the underlying disease is not possible, efforts have to be made to treat the symptom (pruritus) rather than the underlying condition(s).

Without being held to belief, no diagnostic tests exist that reliably can differentiate between histaminergic and non-histaminergic types of pruritus. Therefore, diagnostic efforts have to be focused on the symptom (pruritus) in a similar way as physicians or veterinarians have to determine what type of painkillers to use in a specific patient. Thus, initially, the doctor has to ask the patients or caretakers what medication the patient has used for pruritus in the past. Most important is the question whether antihistaminic drugs have been used successfully. The doctor or veterinarian may also administer antihistaminic drugs before he/she is convinced that the patient is suffering from histaminergic or non-histaminergic pruritus.

One disadvantage of the orally administered drugs that are used to treat pruritus are the systemic side effects that result from their administration. For example, the Generation-1 antihistamines are known to cause sedation upon oral administration. Without being held to theory, it is believed that systemic adverse effects will be less pronounced for drugs that are selectively distributed to specific biophase organs or tissues, e.g., the skin, where the drugs may accumulate in concentrations that are higher than the systemic plasma concentration. Such drugs will reach tissue concentrations that inhibit diseases or symptoms locally in the specific organs or tissues, thereby reducing the systemic exposure of the drug and the incidence of systemic side effects of the drug. Thus, it may be advantageous to use a drug that accumulates at the biophase(s) for a disease or for a specific symptom. Such compounds will selectively express their activities where they are accumulated, while avoiding the adverse effects of more evenly distributed drugs.

It has specifically been found that after oral administration, racemic norketotifen (RS-norketotifen) and both isomers thereof (R-norketotifen, S-norketotifen) accumulate in the skin. The skin is the biophase for numerous dermal diseases and for the symptom called pruritus. The pharmacokinetic exposure parameters—area under the curve, half-lives and mean residence times—of norketotifen in the dermal biophase have been found to significantly exceed the corresponding exposure parameters in the systemic circulation (See Example 6.)

In one embodiment, disclosed herein is a method treating a mammal in need of treatment for non-histaminergic pruritus, comprising orally or topically administering to the mammal in need thereof a therapeutically effective amount of norketotifen. In specific embodiments, the biophase-selective non-histaminergic pruritus inhibitor is RS-, R- or S-norketotifen, or pharmaceutically acceptable salts thereof, specifically RS-norketotifen or pharmaceutically acceptable salts thereof. As used herein, non-histaminergic pruritus is chronic pruritus that is resistant to treatment with selective histamine H-1, H-2 and H-4 receptor inhibitors.

In another aspect, a method of treating non-histaminic pruritus in a patient comprises determining whether said patient suffers from non-histaminic pruritus, and if said determination is positive, orally administering to said patient a therapeutically effective amount of RS-norketotifen or a pharmaceutically acceptable salt thereof, wherein RS-norketotifen or a pharmaceutically salt thereof decrease the itchiness in the patient, and wherein the non-histaminergic pruritus is resistant to treatment with selective histamine H-1-receptor inhibitors, histamine H-2-receptor inhibitors and histamine H-4-receptor inhibitors Disclosed herein is a method for treating a mammal with a type of pruritus, that is not responsive to treatment with selective anti-histaminergic drug, including selective histamine H-1 receptor inhibitors, such as for example diphenhydramine or desloratadine, or selective histamine H-2 receptor inhibitors, such as for example cimetidine or ranitidine, or selective histamine H-4 receptor inhibitors, such as for example JNJ7777120 or JNJ 10191584.

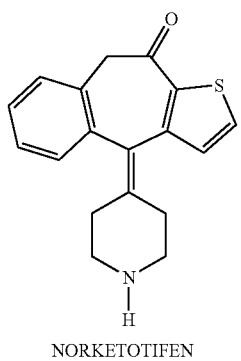 [SMILES: O=C1Cc2ccccc2C(=C2CCNCC2)c2ccsc21]

NORKETOTIFEN

Norketotifen can be made by methods known in the art, as described in U.S. Pat. No. 3,682,930, the disclosure of which is hereby incorporated by reference for its teaching of the synthesis of norketotifen.

The norketotifen isomers can be made as described in U.S. Pat. No. 7,226,934 and U.S. Pat. No. 7,557,128, the disclosures of which are hereby incorporated by reference for their teaching of the synthesis of the norketotifen isomers.

Norketotifen is the active metabolite of ketotifen, which is a Generation-1 (sedative) antihistamine. Ketotifen is the most sedating of all marketed antihistamines. The sedative effects of ketotifen are strictly dose-limiting and doses higher than the recommended dose 1 mg, bid, are rarely used. It is currently believed that approximately 0.5 mg norketotifen is formed in the body for every 1 mg of ketotifen that is systemically administered. The metabolism—demethylation of the piperidine nitrogen in the ketotifen molecule—takes place in the liver, using liver enzymes such as CYP1A2 and CYP3A4. The sedation by ketotifen is caused by the short-acting "pro-drug," which is ketotifen per se, while the therapeutic effects of the orally administered drug are almost exclusively caused by the long-acting metabolite norketotifen.

Repeat-dose pharmacological and toxicological studies have now been performed and it has surprisingly been found that daily doses up to 20 mg/kg/day of racemic or isomeric norketotifen can be given chronically to dogs without causing sedation or other adverse events. Similarly, it has been found that doses up to 10 mg, bid of norketotifen in humans do not produce sedation when tested in human subjects.

Useful oral doses of racemic or isomeric norketotifen to human patients suffering from non-histaminergic pruritus are between 2 mg/day and 500 mg/day. More preferred is a daily oral dose of 2 mg/day to 40 mg/day to a human patient and most preferred is a human dose of 2 mg/day to 20 mg/day of norketotifen or an isomers thereof to human patients suffering from non-histaminergic pruritus. The doses used here refer to norketotifen free base, although various salt forms can be used.

If not stated differently, the term norketotifen herein refers to the free base or to a salt forms thereof. The preferred salts forms are the hydrochloride salt and the hydrogen fumarate salt.

Useful oral doses of racemic or isomeric norketotifen to canine and feline patients suffering from non-histaminergic pruritus are between 0.5 mg/kg bodyweight and 20 mg/kg bodyweight, expressed as free base and dosed once or more times daily.

Useful oral doses of racemic or isomeric norketotifen to equine patients suffering from non-histaminergic pruritus are between 0.2 mg/kg bodyweight and 15 mg/kg bodyweight, expressed as free base and dosed once or more times daily.

Pharmaceutical compositions for oral administration of solid dosage forms include capsules, granules, pills, powders and tablets. In solid dosage forms, the active compound may be mixed with one or more pharmaceutically acceptable excipients or carriers (such as for example sodium citrate, dicalcium phosphate), fillers or extenders (such as for example starch, lactose, sucrose, glucose, mannitol, silicic acid), binders (such as for example carboxymethyl-cellulose, alginates, gelatin, polyvinylpyrrolidone, sucrose, acacia), humectants (such as for example glycerol), solution retarding agents (such as for example paraffin), disintegrating agents (such as for example agar-agar, calcium carbonate, starch, alginic acid, silicates, sodium carbonate), absorption accelerators (such as for example quaternary ammonium compounds), wetting agents (such as for example cetyl alcohol, glycerol monostearate), absorbents (such as for example kaolin, bentonite clay), lubricating agents (such as for example talc, calcium stearate, magnesium stearate, polyethylene glycols, sodium lauryl sulfate), and/or other excipients, such as for example buffering agents. Solid forms of capsules, granules, pills, and tablets can have coatings and/or shells (such as for example enteric coatings) known in the art. The compositions may also be designed to release the active ingredient(s) in a certain part of the gastrointestinal tract or in a controlled release, slow-release or in a delayed-release manner. The active compound(s) can also be micro encapsulated with one or more of the above-mentioned excipients or other suitable excipients.

Liquid dosage forms for oral administration may be preferred administration forms to children suffering from pruritus. Such formulations include for example pharmaceutically acceptable solutions, emulsions, suspensions, syrups and elixirs. The liquid dosage form may also contain excipients known to those skilled in the art of drug formulations, such as for example diluents (such as for example water, other solvents and solubilizing agents, and mixtures thereof), and emulsifiers (such as for example ethanol, isopropyl alcohol, ethyl carbonate, ethyl acetate, benzyl alcohol, benzyl benzoate, propylene glycol, butylene glycol, dimethyl formamide, oils, oleic acid, glycerol, polyethylene glycols, sorbitan fatty esters, and mixtures thereof. An example of a Compositions for topical administration of norketotifen to the skin of all patients include creams, droplets, gels, liquids, ointments, powders, sprays, suspensions, and specific delivery systems such as for examples patches and bandages. In addition to the active compound, the dermal composition may also contain other excipients as known to those skilled in the art. Creams, ointments or gels or solutions may contain 10 mg/ml to 100 mg/ml of norketotifen or an isomer thereof, or a salt of said racemate or isomer, calculated as free base but administered either as a salt or as the free base, and applied once or more times daily to the affected areas. The total dose of the topically applied formulation of norketotifen or an isomer thereof will depend on the actual concentration of the active ingredient in the formulation and the size of the surface being treated. An example of a topical/dermal formulation is described in Example 5.

Pharmaceutical compositions for parenteral injections include pharmaceutically acceptable sterile aqueous or non-aqueous solutions, dispersions, suspensions, emulsions and sterile powders for reconstitution into sterile injectable solutions or dispersions prior to use. Various aqueous and non-aqueous carriers, diluents, solvents and vehicles may be used (such as for example water, ethanol, glycerol, glycol), as well as vegetable oils (such as for example olive oil), and organic esters (such as for example ethyl oleate), or mixtures of various excipients may be used. Fluidity can be maintained by use of coating material such as for example lecithin, by restricting particle size and by use of surfactants.

Parenteral compositions may also contain excipients such as preservatives, wetting agents, emulsifying agents, dispersing agents, antibacterial agents, antifungal agents, isotonic agents, and/or absorption-delaying agents. Absorption-prolonging or absorption-slowing effects may be achieved by injecting a crystalline or amorphous suspension with low water solubility. Delayed absorption may also be obtained by dissolving or suspending the drug in an oil vehicle or by using injectable depot forms (ex. microencapsulated matrices of the drug in biodegradable polymers, such as polylactide-polyglycolide, polyorthoesters, polyanhydrides) or by using various types of liposomes or microemulsions to hold the drug. Formulations for injection can be sterilized by various methods.

All compositions may include other excipients as known to those skilled in the art.

The oral or dermal compositions described here can also consist of combination therapies, include norketotifen or an isomer or a salt thereof together with other drugs with antipruritic activity, such as for example a corticosteroid or an immune-suppressant drug. Due to the antipruritic activity of norketotifen or the isomers thereof, a beneficial steroid-sparing or immune-suppressant drug-sparing effect can be obtained when treating patients suffering from various types of pruritic disorders with said combination therapies.

The actual dosage levels of active ingredients in the pharmaceutical compositions disclosed herein may be varied so as to obtain the desired therapeutic effect. Thus the amount of drug used and the frequency of dosing varies and will depend on factors such as the administration form, the severity of the disease and other circumstances, such as for example the general health, age, and weight of the individual patient. Those skilled in the art of medicine will realize that higher or lower doses than those indicated here may be used and the doses may be given more or less frequently than suggested here.

EXAMPLES

The invention is further illustrated by the following non-limiting examples.

Example 1

Non-Histaminergic Antipruritic Activity: Chloroquine-Induced Pruritus in Mice

The objective was to study non-histaminergic antipruritic effects of norketotifen in mice. Chloroquine induces non-histaminergic pruritus in mice.

After fasting for 1.5 hours, mice were administered a single oral dose of the test articles. Sixty minutes after oral dosing, a subcutaneous injection of CQ, 10 mg/kg was administered into the previously shaved rostral part of the back at the interscapular level. Immediately after the CQ injection, the bouts of scratching were counted for 40 minutes by laboratory personnel who were unaware of the drug treatment.

TABLE 2

Antipruritic activity in mice; chloroquine-induced pruritus

| Test Articles (one single oral dose) | N | Bouts/40 min Mean ± SEM | Protection (%) |
|---|---|---|---|
| Vehicle for norketotifen, prednisolone and desloratadine | 16 | 260 ± 35 | — |
| Norketotifen HF 3 mg/kg | 7# | 171 ± 36 | 34 |
| Norketotifen HF 30 mg/kg | 8 | 105 ± 29** | 60 |
| Norketotifen HF 100 mg/kg | 8 | 44 ± 16*** | 83 |
| Prednisolone 30 mg/kg | 8 | 146 ± 11* | 44 |
| Desloratadine 30 mg/kg | 8 | 298 ± 53 | 0 |
| Vehicle for JNJ 7777120 | 8 | 201 ± 34 | — |
| JNJ 7777120 30 mg/kg | 8 | 172 ± 24 | 14 |

HF = hydrogen fumarate (salt)
one outlier was excluded
*Means P ≤ 0.05;
**means P ≤ 0.001;
***means P ≤ 0.0001
Protection was calculated as percent of vehicle events The results demonstrate that single oral doses of norketotifen reduced CQ-induced pruritus in mice. Single-dose prednisolone also reduced CQ-induced pruritus. The histamine H-1 receptor inhibitors desloratadine and JNJ7777120 (H-4) did not inhibit chloroquine-induced pruritus, which confirms reports of poor or no antipruritic activity of histamine H-1 receptor inhibitors in human malaria patients administered chloroquine.

The finding that norketotifen is a potent inhibitor of chloroquine-induced pruritus is surprising since ketotifen has been described as not having inhibitory activity against chloroquine-induced pruritus.

Example 2

Non-Histaminergic Antipruritic Activity: Chloroquine-Induced Pruritus in Dogs The objective was to study non-histaminergic antipruritic effects of norketotifen in dogs. Chloroquine induces non-histaminergic pruritus in dogs.

A new method for testing non-histaminergic antipruritic drug activities in dogs was developed. Chloroquine (CQ) was used as non-histaminergic pruritogen. After fasting for 2 hours, beagle dogs were dosed po with capsules containing the test article. One single dose of norketotifen was administered to the dogs. Immediately thereafter, chloroquine was given intravenously into a cephalic vein (2 mg/kg over 5 minutes). Starting 3 hours after the chloroquine injection, pruritic events (Biting, Licking and Scratching) were counted for 60 minutes. All test articles were administered in gelatin capsules. The pruritic events were counted by laboratory personnel who were unaware of the drug treatment of the animals.

After administration to dogs, CQ induced pruritus that was decreased by norketotifen and prednisolone. Separate chloroquine tests demonstrated the lack of antipruritic activity of the histamine H-1 antagonist desloratadine.

TABLE 3

Antipruritic activity in dogs; chloroquine-induced pruritus

| Test Article | N | Pruritic Events Biting | Licking | Scratching | All Pruritic Events | Protection (%) |
|---|---|---|---|---|---|---|
| Vehicle Control #) | 15 | 18 ± 5 | 40 ± 8 | 36 ± 7 | 94 ± 12 | — |
| Norketotifen 5 mg/kg | 8 | 15 ± 4 | 37 ± 6 | 8 ± 2 | 60 ± 8 | 36 |
| Norketotifen 10 mg/kg | 8 | 11 ± 4 | 20 ± 4 | 2 ± 1 | 33 ± 8** | 65 |
| Norketotifen 20 mg/kg | 8 | 4 ± 2 | 17 ± 4 | 1 ± 0.5 | 22 ± 5*** | 77 |
| Prednisolone 10 mg/kg | 8 | 13 ± 4 | 41 ± 6 | 4 ± 1 | 58 ± 6* | 38 |

) one outlier was excluded.
Protection was calculated as percent of vehicle events.
Means ± SEM
*$P \leq 0.05$; $P \leq 0.01$; *$P \leq 0.001$ when compared with the Vehicle Control group.

The results demonstrate that norketotifen decreased chloroquine-induced pruritus, within three hours after a single oral dose of the compound. Prednisolone is known to inhibit pruritus in dogs with AD and is also known to reduce chloroquine-induced pruritus in malaria patients. The antipruritic activity of prednisolone in this study validated this test method.

Justification of the model: CQ induces pruritus by activating MrgprA3 (Mas-related G-protein Ankyrin) receptors, which are expressed in dermal, afferent dendrites of dorsal root ganglia. The ligand-activated calcium channels TRPA1 (Transient Receptor Potential Ankyrin 1) and TRPV1 (Transient Receptor Potential Vanilloid 1) are the downstream targets for MrgprA3 and at least one of TRPA1 and TRPV1 is currently believed to be required for chronic itch that is caused by non-histaminergic atopic dermatitis. IL-31 receptors are co-localized with the receptors TRPA1 and TRPV1 and the IL-31 dependence is obvious from the fact that IL-31-induced pruritus is reduced in receptor knockout mice. Thus, CQ-induced pruritus is a well-justified dog model for tests of effects of drugs on non-histaminergic AD-pruritus. Without being held to theory, inhibition of the MrgprA3/TRPA1 axis may be a clinically relevant non-histaminergic mode of action of norketotifen.

Example 3

Non-Histaminergic Antipruritic Activity: Leukotriene-Induced Pruritus in Mice Antipruritic effects were tested in vivo in CD-1 mice and the leukotriene precursor 5-HPETE was used as the pruritogen to induce non-histaminergic pruritus. The animals were dosed orally with norketotifen HF, 10 mg/kg, and sixty minutes thereafter, 5-HPETE (5 μg in 50 μL saline with 0.1% ethanol) was injected intradermally into the previously clipped area of the rostral part of the back of the mice. Starting immediately after the 5-HPETE injections, the bouts of scratchings were counted for 40 minutes. Protection against pruritus was calculated in % of the vehicle effect.

The test results (Table 4) demonstrated that norketotifen HF, 10 mg/kg, po reduced 5-HPETE-induced pruritus in mice by about 40%.

Separate 5-HPETE tests demonstrated the absence of antipruritic activity of the histamine H-1 antagonist desloratadine.

TABLE 4

Antipruritic activity in mice; 5HPETE-induced pruritus Means ± SEM.

| Test Article | N | Bouts/ 40 min | Protection (%) |
|---|---|---|---|
| Vehicle for Norketotifen HF* | 8 | 58.6 ± 5.0 | — |
| Norketotifen HF 10 mg/kg | 6 | 34.2 ± 9.1** | 42 |

*HF = hydrogen fumarate salt
**$P \leq 0.05$

It was found that 5-HPETE is a potent inducer of non-histaminergic pruritus. Norketotifen inhibited 5-HPETE-induced pruritus within one hour after the oral administration of a single dose of 10 mg/kg norketotifen to mice.

Justification of the model: It has been shown that HPETE and other lipoxygenase products directly activate the TRPA1 and TRPV1 ligand-activated calcium channels on dorsal root ganglia, which may explain the non-histaminergic pruritic activity of 5-HPETE.

Example 4

Non-Histaminergic Antipruritic Activity: IL-31 Induced Pruritus in Mice

Increased dermal concentration of the pruritogenic cytokine IL-31 with concomitant non-histaminergic pruritus is found in the skin of human and canine patients with atopic dermatitis (AD). It is well known that pruritus of patients suffering from AD is not inhibited by histamine H-1 inhibitors, like desloratadine, although Generation-1 antihistamines, like diphenhydramine, may offer some pruritic relief for AD-patients, due to their soporific activity.

The present studies were performed in mice, using murine IL31 as the pruritogen to induce non-histaminergic pruritus. The mice were dosed orally (po) with a test article, exactly 60 min before murine IL31 at a dose of 1.0 µg/30 gram mouse was injected subcutaneously (sc) into a previously depilated area on the rostral part of the back of mice. IL31 was dissolved in phosphate buffered saline (PBS) with 0.1% bovine serum albumin (BSA). The injected volume was 0.1 ml/mouse. The bouts of scratchings were counted, starting 30 min after the injection of IL-31 and lasting for a total of 120 min. The bouts of scratchings were counted by laboratory personnel, who were not aware of the pretreatment of the animals.

Separate IL-31 tests using the methodology described above demonstrated the absence of antipruritic activity of the histamine H-1 antagonist desloratadine 10 mg/kg, po.

The test results demonstrated antipruritic activity of norketotifen and the reference compound oclacitinib, is shown in Table 5.

TABLE 5

Non-histaminergic antipruritic activity in mice; IL31-induced pruritus

| Test Article | N | Pruritic Bouts Mean ± SEM | Protection (%) |
| --- | --- | --- | --- |
| Vehicle | 8 | 203 ± 45 | — |
| Norketotifen HF 10 mg/kg | 8 | 93 ± 10* | 54 |
| Oclacitinib maleate 10 mg/kg | 8 | 116 ± 29 | 43 |

*means P ≤ 0.05 when compared with Vehicle.
HF = hydrogen fumarate (salt)

It was concluded that a single dose of norketotifen potently inhibited IL-31-induced pruritus by non-histaminergic mechanisms within one hour after oral administration.

IL-31 is a non-histaminergic and highly pruritic cytokine that is a key mediator for pruritus that is caused by both allergic dermatitis and non-allergic dermatitis. High concentrations of the potently pruritic cytokine IL-31 have been found not only in the skin from patients with atopic dermatitis and non-atopic dermatitis but also in the skin from patients suffering from alopecia areata, mycosis fungoides, notalgia paresthetica, prurigo nodularis, psoriasis and Sézary syndrome, all of which are dermal diseases causing pruritus. Thus, pruritus expressed in patients suffering from these diseases suffer from IL-31-mediated, non-histaminergic pruritus.

The problem is that few drugs inhibit the pruritogenic effects of IL-31. The only presently known IL-31 selective inhibitor is OSMR-L-GLP, which is a fusion protein consisting of 720 amino acids. In addition, while antibodies to IL-31 and the IL-31 receptor can be expected to selectively interrupt the IL-31 pruritogenic pathway, these molecules are also proteins that will have to be injected. Thus, the currently available selective IL-31 inhibitors are not suitable for oral or topical administration. Oclacitinib, which is a Janus kinase inhibitor, inhibits the pruritogenic effects of IL-31, however, it has only been approved for veterinary use in dogs. It has now surprisingly been found that norketotifen inhibits IL-31-mediated pruritus (See Table 5).

Example 5

Topical Administration of Norketotifen

The objective of this study was to determine if norketotifen is absorbed after topical (dermal) application.

A lanolin/ethanol cram containing 1.0% norketotifen HF was prepared as follows: A solution containing 2.5% of RS-norketotifen hydrogen fumarate, calculated as free base free base in ethanol was prepared. Lanolin was weighed and liquefied by submerging a vessel containing lanolin in hot water. While the lanolin was a liquid, it was rapidly mixed (by vortexing) with the 2.5% of RS-norketotifen solution in ethanol to result in a 1.0% solution. The ethanol/lanolin solution was allowed to solidify resulting in a cream which consisted of 1.0% RS-norketotifen in 60% lanolin/40% ethanol.

About 10 mg of either norketotifen cream or a vehicle cream was applied to both ears of mice and left for 30 minutes. The cream was then removed and a solution of 1% of the known pro-inflammatory compound croton oil in acetone was applied to both ears. After the acetone had dried (10 seconds), the cream containing the test article (or vehicle) was reapplied and the animals were returned to their cages. At 0, 30, 60, 90 and 120 minutes following the croton oil administration, groups of four animals were anesthetized with halothane and euthanized. Cream was wiped off from the ears and ears were removed and weighed.

The effects of the test article are shown in Table 6. All results represent mean ear weights (±S.E.M.) from 8 ears. The weight of the croton oil treated ears was increased by about 30 percent within 90 minutes. There was complete inhibition of the croton oil-induced inflammation after a single dermal dose of norketotifen. It was concluded that norketotifen was rapidly absorbed after topical/dermal application. The very rapid onset (<30 min) indicates that the skin is the biophase for the anti-pruritic activity of norketotifen.

TABLE 6

Effects of norketotifen cream on dermal inflammation in mice.

| Time after Croton Oil Application (min) | Average Ear Weight (mg) ± S.E.M. | |
| --- | --- | --- |
| | Vehicle | RS-Norketotifen |
| 0 (predose) | 35 ± 1 | 36 ± 1 |
| 30 | 41 ± 1 | 36 ± 1 |
| 60 | 41 ± 1 | 37 ± 2 |
| 90 | 46 ± 2 | 36 ± 2 |

It was concluded that norketotifen was rapidly absorbed after topical/dermal application. The very rapid onset (<30 min) indicates that the skin is the biophase for the anti-pruritic activity of norketotifen.

Example 6

Dermal Drug Accumulation after Oral Drug Administration

The objective of this study was to determine pharmacokinetic properties of norketotifen after oral administration.

Five male beagle dogs, weighing 11.2-13.9 kg (2-4 years old) were used in the study. All animals were administered gelatin capsules containing oral doses of the test article 8.0 mg/kg/day as a hydrogen fumarate salt, equal to 5.6 mg/kg/day of the free base. The animals were dosed once daily for four consecutive weeks followed by daily observations for an additional two-week washout period. Multiple plasma samples and skin biopsies were taken from each dog on Day 1 and Day 28 of drug administration. The plasma and skin samplings were performed at pre-dose, and at 2, 6, 12 and 24 hours post-dose. Plasma and skin samples were also taken intermittently at predetermined intervals during the 28-days dosing period and up to the last day of the study, which was Day 42. Blood samples were taken from v. cephalica antebrachii. Skin biopsies were taken from the area between the mid ventral to lateral abdominal areas, using a 6 mm (diameter) skin biopsy device (Acu-Punch®, Acuderm® Inc., Fort Lauderdale, Fla. 33309). Multiple plasma and biopsy samples were obtained from each of 4 or 5 dogs. Subcutaneous fat deposits were carefully trimmed from the skin samples and the skin samples were weighed. The plasma samples and skin biopsy samples were analyzed using validated LC/MS/MS methodology. All pharmacokinetic analyses were performed using Pharsight WinNonlin® Professional v5.2.1 software.

As shown in Table 7, there was a pronounced dermal accumulation of norketotifen after oral drug administration.

TABLE 7

Pharmacokinetic (PK) Parameters on Day 28 of Dosing.

| PK Parameter | S-BPI Plasma | S-BPI Skin | R-BPI Plasma | R-BPI Skin | RS-BPI Plasma | RS-BPI Skin |
|---|---|---|---|---|---|---|
| $AUC_{0-\infty}$ | 1627 | 25710 | 1658 | 20376 | 3286 | 54187 |
| $t_{1/2}$ (hr) | 10.9 | 162.7 | 7.7 | 157.0 | 10.5 | 167.6 |
| MRT (hr) | 11.3 | 159.0 | 14.1 | 159.1 | 12.8 | 169.3 |

$AUC_{0-\infty}$ = Area under the plasma concentration (or skin concentration) vs. time curves
$t_{1/2}$ = Plasma or skin half-life
MRT = Mean residence time
S-BPI = S-norketotifen;
R-BPI = R-norketotifen;
RS-BPI = total norketotifen Since norketotifen is a potent inhibitor of pruritus, and since the skin is the biophase for that activity, the dermal accumulation of norketotifen will further improve the anti-pruritic activity of this drug, while simultaneously decreasing the risk for systemic adverse events.

Example 7

Exemplary Oral Dosage Formulations

Formulations for oral administration of norketotifen (such as for example tablets, capsules and syrups) have been developed.

TABLE 8

Tablet formulations

| Ingredient | Amount per tablet | Amount per batch |
|---|---|---|
| Norketotifen | 10 mg | 100 g |
| MCC* | 30 mg | 300 g |
| Lactose | 70 mg | 700 g |
| Calcium stearate | 2 mg | 20 g |
| FD&C Blue #1 Lake** | 0.03 mg | 300 mg |

*MCC = microcrystalline cellulose;
**FD&C Blue No 1 Aluminum Lake is a FDA-approved color for tablets The active ingredient is blended with the lactose and the microcrystalline cellulose until a uniform blend is formed. The blue lake is added and further blended. Finally, the calcium stearate is blended in, and the resulting mixture is compressed into tablets using for example a 9/32-inch (7 mm) shallow concave punch. Tablets of other strengths may be prepared by altering the ratio of active ingredient to the excipients or to the final weight of the tablet.

Those skilled in the art realize that oral formulations can be in the form of, for example, a tablet, a capsule, a dog-treat, a cat-treat, a syrup or another form of liquid formulations.

Example 8

Exemplary Topical/Dermal Dosage Formulations

Topical/dermal solutions, topical/dermal ointments, topical/dermal emulsions and topicaldermal creams are examples of topical/dermal administration forms of RS-norketotifen. Preservative excipients will not be needed since norketotifen formulations are self-preserving.

TABLE 9

Examples of topical/dermal solutions formulations containing norketotifen.

| | Excipients in per cent | | |
|---|---|---|---|
| | 1008 | 1009 | S1010 |
| Norketotifen HF (%) | 1.0 | 1.0 | 1.0 |
| Sodium phosphate dibasic | 0.473 | — | 0.160 |
| Sodium phosphate monobasic, monohydrate | 0.460 | — | — |
| NaCl | 0.480 | — | — |
| Sodium citrate | — | 0.300 | — |
| Propylene glycol | — | 1.750 | — |
| Methylcellulose | — | — | 0.500 |
| Glycerin | — | — | 2.400 |
| Water | q.s. | q.s. | q.s. |
| pH | 4.6-6.5 | 4.6-6.5 | 4.6-6.5 |

If needed, the viscosity can be adjusted by a viscosity-modifying agent to obtain the preferred viscosity. The final acidity can be adjusted by adjusting the concentrations of buffering agents or by adding an acid or a base.

The topical/dermal solution formulations were prepared by adding the excipients, one at a time to an appropriate amount of water, followed by mixing until dissolved. Once all excipients had been added and dissolved, norketotifen was added to the solution of excipients and mixed continuously until dissolved. The acidity of the topical/dermal solutions was measured and adjusted by modifying the buffer system or by adding an acid or a base solution to the desired pH. If needed, viscosity and tonicity were adjusted as indicated above.

The use of the terms "a" and "an" and "the" and similar referents (especially in the context of the following claims) are to be construed to cover both the singular and the plural, unless otherwise indicated herein or clearly contradicted by context.

The terms first, second etc. as used herein are not meant to denote any particular ordering, but simply for convenience to denote a plurality of, for example, layers.

The terms "comprising", "having", "including", and "containing" are to be construed as open-ended terms (i.e., meaning "including, but not limited to") unless otherwise noted.

Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable.

All methods described herein can be performed in a suitable order unless otherwise indicated herein or otherwise clearly contradicted by context.

The use of any and all examples, or exemplary language (e.g., "such as"), is intended merely to better illustrate the invention and does not pose a limitation on the scope of the invention unless otherwise claimed.

No language in the specification should be construed as indicating any non-claimed element as essential to the practice of the invention as used herein.

The term "antihistamine" as used herein refers to histamine H-1 receptor inhibitors unless stated differently.

The terms "Generation-1 antihistamine" and "Gen-1 antihistamine" as used herein refers to antihistamines that commonly express sedative effects The terms "Generation-2 antihistamine" and Gen-2 antihistamine" as used herein refers to antihistamines that commonly do not express sedative effects The term "patient" as used herein refers to human patients, canine patients, feline patients and equine patients unless stated differently.

As used herein, the term "biophase" refers to the site(s) in the body of patients, where a drug expresses its therapeutic activity.

For the sake of simplicity the terms "dermatitis" and "eczema" are used inter-changeably and used as synonyms herein.

The terms "disease", "condition" and "disorder" are synonyms and are used interchangeably herein.

The terms "atopic" and "allergic" are synonyms and are used interchangeably herein.

The terms "histaminic" and "histaminergic" are synonyms and are used interchangeably herein.

The terms "non-histaminic" and "non-histaminergic" are synonyms and are used interchangeably herein While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from essential scope thereof. Therefore, it is intended that the invention not be limited to the particular embodiment disclosed as the best mode contemplated for carrying out this invention, but that the invention will include all embodiments falling within the scope of the appended claims.

The invention claimed is:

1. A method of treating a mammal in need of treatment for non-histaminic pruritus, comprising orally administering to the mammal in need thereof a therapeutically effective amount of RS-norketotifen or a pharmaceutically acceptable salt thereof, thereby reducing the desire to scratch in the mammal, wherein the non-histaminergic pruritus is resistant to treatment with selective histamine H-1-receptor inhibitors, histamine H-2-receptor inhibitors and histamine H-4-receptor inhibitors, and wherein the non-histaminergic pruritus is associated with a dermal disorder that is alopecia areata, asteatotic dermatitis, atopic dermatitis, cutaneous B-cell lymphoma, cutaneous T-cell lymphoma, dermatitis herpetiformis, discoid eczema, hand eczema, ichthyosis, idiopathic dermatitis, mycosis fungoides, non-atopic dermatitis, notalgia paresthetica, psoriasis, prurigo nodularis, seborrheic dermatitis, Sézary syndrome or varicose eczema.

2. The method of claim 1, wherein said mammal is a human.

3. The method of claim 1, wherein said mammal is a dog.

4. The method of claim 1, wherein said mammal is a cat.

5. The method of claim 1, wherein said mammal is a horse.

6. A method of treating non-histaminic pruritus in a patient, comprising determining whether said patient suffers from non-histaminic pruritus and if said determination is positive, orally administering to said patient a therapeutically effective amount of RS-norketotifen or a pharmaceutically acceptable salt thereof, wherein RS-norketotifen or a pharmaceutically acceptable salt thereof decrease the itchiness in the patient, and wherein the non-histaminergic pruritus is resistant to treatment with selective histamine H-1-receptor inhibitors, histamine H-2-receptor inhibitors and histamine H-4-receptor inhibitors, and wherein the non-histaminergic pruritus is associated with a dermal disorder that is alopecia areata, asteatotic dermatitis, atopic dermatitis, cutaneous B-cell lymphoma, cutaneous T-cell lymphoma, dermatitis herpetiformis, discoid eczema, hand eczema, ichthyosis, idiopathic dermatitis, mycosis fungoides, non-atopic dermatitis, motalgia paresthetica, psoriasis, prurigo nodularis, seborrheic dermatitis, Sézary syndrome or varicose eczema.

7. The method of claim 6, wherein said mammal is a human.

8. The method of claim 6, wherein said mammal is a dog.

9. The method of claim 6, wherein said mammal is a cat.

10. The method of claim 6, wherein said mammal is a horse.

* * * * *